United States Patent
Kim et al.

(10) Patent No.: US 11,699,784 B2
(45) Date of Patent: Jul. 11, 2023

(54) CATHODE ACTIVE MATERIAL FOR LITHIUM SECONDARY BATTERY AND METHOD OF MANUFACTURING THE SAME

(71) Applicant: SK INNOVATION CO., LTD., Seoul (KR)

(72) Inventors: Jik Soo Kim, Daejeon (KR); Sang Bok Kim, Daejeon (KR); Hyo Shin Kwak, Daejeon (KR); Myoung Lae Kim, Daejeon (KR); Se Rah Moon, Daejeon (KR); Jin Seok Seo, Daejeon (KR); Mi Jung Noh, Daejeon (KR); Duck Chul Hwang, Daejeon (KR)

(73) Assignee: SK ON CO., LTD., Seoul (KR)

( * ) Notice: Subject to any disclaimer, the term of this patent is extended or adjusted under 35 U.S.C. 154(b) by 441 days.

(21) Appl. No.: 16/674,864

(22) Filed: Nov. 5, 2019

(65) Prior Publication Data
US 2020/0144612 A1    May 7, 2020

(30) Foreign Application Priority Data

Nov. 6, 2018 (KR) .................. 10-2018-0135346
Oct. 10, 2019 (KR) .................. 10-2019-0125433

(51) Int. Cl.
  *H01M 4/36* (2006.01)
  *H01M 4/525* (2010.01)
  (Continued)

(52) U.S. Cl.
  CPC .......... *H01M 4/366* (2013.01); *C07D 277/36* (2013.01); *C07D 295/14* (2013.01); *H01M 4/525* (2013.01);
  (Continued)

(58) Field of Classification Search
  CPC ...... H01M 4/366; H01M 4/525; H01M 4/628; H01M 10/0525
  See application file for complete search history.

(56) References Cited

U.S. PATENT DOCUMENTS

| | | | |
|---|---|---|---|
| 5,510,212 A * | 4/1996 | Delnick ................ | H01M 4/587 264/29.7 |
| 2015/0243970 A1 * | 8/2015 | Choi ..................... | H01M 4/366 429/231.95 |

(Continued)

FOREIGN PATENT DOCUMENTS

| CN | 1622367 A | 6/2005 |
|---|---|---|
| CN | 104733785 A | 6/2015 |

(Continued)

OTHER PUBLICATIONS

First Office Action issued by the CNIPA dated Dec. 20, 2021.
(Continued)

*Primary Examiner* — Jayne L Mershon
(74) *Attorney, Agent, or Firm* — IP & T Group LLP

(57) ABSTRACT

A cathode active material for a lithium secondary battery includes a lithium metal oxide particle and a thio-based compound formed on at least portion of a surface of the lithium metal oxide particle. The thio-based compound has a double bond that contains a sulfur atom. Chemical stability of the lithium metal oxide particle may be improved and surface residues may be reduced by the thio-based compound.

9 Claims, 3 Drawing Sheets

(51) Int. Cl.
  *H01M 10/0525* (2010.01)
  *H01M 4/62* (2006.01)
  *C07D 295/14* (2006.01)
  *C07D 277/36* (2006.01)
  *H01M 4/02* (2006.01)

(52) U.S. Cl.
  CPC ....... *H01M 4/628* (2013.01); *H01M 10/0525* (2013.01); *H01M 2004/028* (2013.01)

(56) References Cited

U.S. PATENT DOCUMENTS

| | | | |
|---|---|---|---|
| 2015/0340686 A1† | 11/2015 | Sun | |
| 2016/0204466 A1 | 7/2016 | Nogami et al. | |
| 2016/0204467 A1† | 7/2016 | Nogami | |
| 2020/0067089 A1* | 2/2020 | Shinpuku | H01M 10/0525 |

FOREIGN PATENT DOCUMENTS

| | | | |
|---|---|---|---|
| CN | 105849967 A | | 8/2016 |
| JP | 07092148 A | | 4/1995 |
| JP | 2001297768 A | | 10/2001 |
| JP | 2002170564 A | | 6/2002 |
| JP | 2013-152926 | | 8/2013 |
| JP | 2018-152329 | | 9/2018 |
| KR | 10-0821523 | | 4/2008 |
| KR | 10-1014111 | | 2/2011 |
| KR | 10-1050333 | | 7/2011 |
| KR | 10-2015-0104675 A | | 9/2015 |
| KR | 10-2016-0038294 | | 4/2016 |
| KR | 10-2017-0080483 A | | 7/2017 |
| KR | 10-2018-0010287 A | | 1/2018 |
| KR | 10-2018-0071106 | | 6/2018 |
| WO | 2018/172272 A1 | | 9/2018 |

OTHER PUBLICATIONS

Office Action issued by the Korean Intellectual Property Office dated Nov. 2, 2020.
Notice of Allowance for the Chinese Patent Application No. 202110071212.9 issued by the Chinese Patent Office dated May 18, 2023.

\* cited by examiner
† cited by third party

CATHODE ACTIVE MATERIAL FOR LITHIUM SECONDARY BATTERY AND METHOD OF MANUFACTURING THE SAME

CROSS-REFERENCE TO RELATED APPLICATION AND CLAIM OF PRIORITY

This application claims priority to Korean Patent Applications No. 10-2018-0135346 filed on Nov. 6, 2018 and No. 10-2019-0125433 filed on Oct. 10, 2019 in the Korean Intellectual Property Office (KIPO), the entire disclosure of which is incorporated by reference herein.

BACKGROUND

1. Field

The present invention relates to a cathode active material for a lithium secondary battery and a method of manufacturing the same. More particularly, the present invention relates to a lithium metal oxide-based cathode active material for a lithium secondary battery and a method of manufacturing the same.

2. Description of the Related Art

A secondary battery which can be charged and discharged repeatedly has been widely employed as a power source of a mobile electronic device such as a camcorder, a mobile phone, a laptop computer, etc., according to developments of information and display technologies. Recently, the secondary battery or a battery pack including the same is being developed and applied as an eco-friendly power source of an electric automobile such as a hybrid vehicle.

The secondary battery includes, e.g., a lithium secondary battery, a nickel-cadmium battery, a nickel-hydrogen battery, etc. The lithium secondary battery is highlighted due to high operational voltage and energy density per unit weight, a high charging rate, a compact dimension, etc.

For example, the lithium secondary battery may include an electrode assembly including a cathode, an anode and a separation layer, and an electrolyte immersing the electrode assembly. The lithium secondary battery may further include an outer case having, e.g., a pouch shape.

A lithium metal oxide may be used as a cathode active material of the lithium secondary battery, and a nickel-based lithium metal oxide may be used as the lithium metal oxide.

As an application of the lithium secondary battery has been expanded, demands of more improved life-span, capacity and operation stability are increased. In the lithium metal oxide used as the cathode active material, non-uniformity of a chemical structure due to lithium precipitation may be caused, and the lithium secondary battery having desired capacity and life-span may not be obtained. Further, a structure of the lithium metal oxide may be transformed or damaged when charging and discharging operations are repeated to degrade life-span stability and capacity retention.

For example, Korean Published Patent Application No. 10-0821523 discloses a method of removing lithium salt impurities by washing a lithium complex metal oxide with water. However, the impurities may not be sufficiently removed by the method, and surface damages of cathode active material particles may be caused during the washing process.

SUMMARY

According to an aspect of the present invention, there is provided a cathode active material for a lithium secondary battery having improved operational stability, and electrical property and a method of manufacturing the same.

According to an aspect of the present invention, there is provided a lithium secondary battery having improved operational stability and electrical property.

According to exemplary embodiments, a cathode active material for a lithium secondary battery includes a lithium metal oxide particle and a thio-based compound formed on at least portion of a surface of the lithium metal oxide particle, the thio-based compound having a double bond that contains a sulfur atom.

In some embodiments, the thio-based compound may include at least one of a thioamide compound represented by Structural Formula 1, a tri-thiocarbonate compound represented by Structural Formula 2 or a thiosulfate compound including a thio-sulfate ion represented by Structural Formula 3.

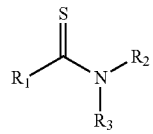

[Structural Formula 1]

In the structural Formula 1 above, $R_1$ may represent hydrogen, halogen, a salt containing $O^-$ or $S^-$, a C1-C10 hydrocarbon group capable of substituted with a substituent group, a C1-C10 alkoxy group, an amine group, an amine group substituted with a C1-C10 alkyl group, a C1-C10 thioalkyl group or a thioamide group, $R_2$ and $R_3$ may be each independently hydrogen or a C1-C10 hydrocarbon group capable of substituted with a substituent group, $R_2$ and $R_3$ may be capable of being fused together to form a ring, and the substituent group capable of being combined with $R_1$, $R_2$ and $R_3$ may include halogen, a cyano group, a hydroxyl group or a carboxyl group,

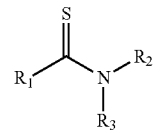

[Structural Formula 2]

In the structural Formula 2 above, $R^1$ and $R^2$ may each independently represent hydrogen or a C1-C10 hydrocarbon group capable of substituted with a substituent group, $R^1$ and $R^2$ may be capable of being fused together to form a ring, and the substituent group capable of being combined with $R^1$ and $R^2$ includes halogen, a cyano group, a hydroxyl group or a carboxyl group.

$(S=SO_3)^{-2}$  [Structural Formula 3]

In some embodiments, the salt containing $O^-$ or $S^-$ included in $R_1$ may be a salt with an alkaline metal cation, an alkaline earth metal cation, $N^+R_4$ or $P^+R_4$, and $R_4$ may be hydrogen or a C1-C8 alkyl group.

In some embodiments, the hydrocarbon group included in $R_1$, $R_2$ and $R_3$ may be substituted or connected by at least one selected from a group consisting of a carbon-carbon double bond, —O—, —S—, —CO—, —OCO—, —SO—, —CO—O—, —O—CO—O—, —S—CO—, —S—CO—O—, —CO—NH—, —NH—CO—O—, —NR'—, >P=O, —S—S— and —SO$_2$—, and R' may be hydrogen or a C1-C8 alkyl group.

In some embodiments, the thioamide compound may include at least one selected from a group consisting of compounds represented by Chemical Formulae 1 to 19.

[Chemical Formula 1]

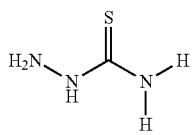

[Chemical Formula 2]

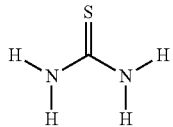

[Chemical Formula 3]

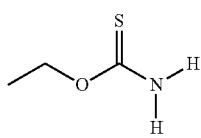

[Chemical Formula 4]

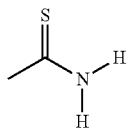

[Chemical Formula 5]

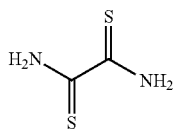

[Chemical Formula 6]

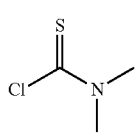

[Chemical Formula 7]

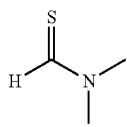

[Chemical Formula 8]

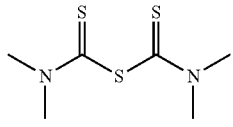

[Chemical Formula 9]

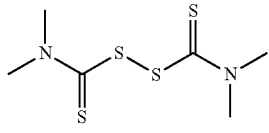

[Chemical Formula 10]

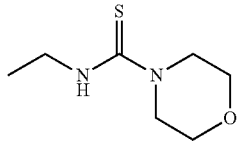

[Chemical Formula 11]

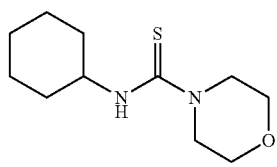

[Chemical Formula 12]

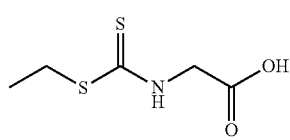

[Chemical Formula 13]

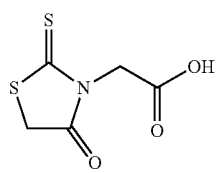

[Chemical Formula 14]

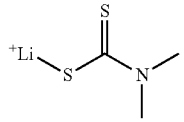

[Chemical Formula 15]

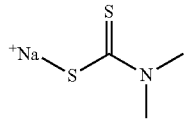

[Chemical Formula 16]

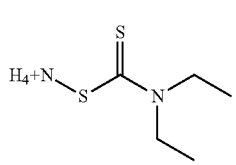

[Chemical Formula 17]

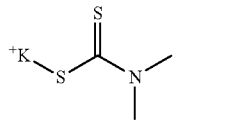

[Chemical Formula 18]

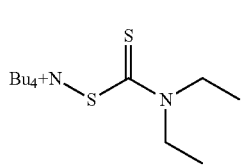

[Chemical Formula 19]

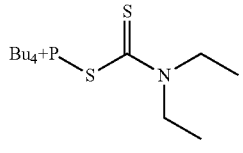

In some embodiments, the tri-thiocarbonate compound may include at least one of a compound represented by Chemical Formula 20 or a compound represented by Chemical Formula 21.

[Chemical Formula 20]

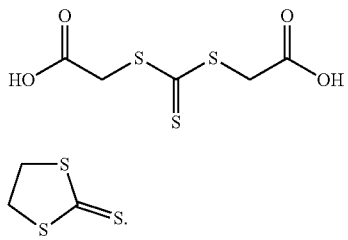

[Chemical Formula 21]

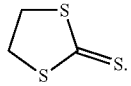

In some embodiments, the thiosulfate compound may include at least one selected from a group consisting of salts represented by Chemical Formulae 22 to 24.

[Chemical Formula 22]

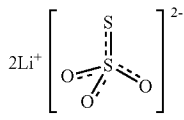

[Chemical Formula 23]

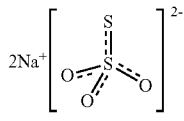

[Chemical Formula 24]

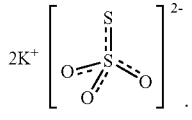

In some embodiments, the lithium metal oxide particle may include a nickel-based lithium oxide represented by General Formula 1 below.

$Li_xNi_yM_{1-y}O_2$  [General Formula 1]

In the General Formula 1 above, $0.95 \leq x \leq 1.08$, $y \geq 0.5$, and M may be at least one element selected from a group consisting of Co, Mn, Al, Zr, Ti, B, Mg or Ba.

In some embodiments, in the General Formula 1, $0.8 \leq y \leq 0.93$.

In some embodiments, in the General Formula 1, M may include Co and Mn.

In some embodiments, the lithium metal oxide particle may include a doping or a coating which may contain at least one of Al, Zr or Ti.

In some embodiments, the thio-based compound may form a coating layer, a ligand bond or a complex bond on the surface of the lithium metal oxide particle.

In some embodiments, the lithium metal oxide particle may have a layer structure, and a grain boundary at a surface portion of the lithium metal oxide particle may be coated by the thio-based compound.

According to exemplary embodiments, a cathode active material for a lithium secondary battery includes a lithium metal oxide particle and a thiosulfate anion ($S_2O_3^{2-}$) formed on at least portion of a surface of the lithium metal oxide particle. A content of the thiosulfate anion of the lithium metal oxide particle measured by an ion chromatography analysis is in a range from 100 ppb to 8,000 ppb.

In some embodiments, a surface component represented by General Formula 2 may be detected by a Time of Flight Secondary Ion Mass Spectrometry (TOF-SIMS) analysis on the surface of the lithium metal oxide particle.

$M1_xC_yH_zS_aO_b$  [General Formula 2]

In the General Formula 2 above, M1 is an alkali metal or an alkali earth metal, $x \geq 0$, $y \geq 0$, $z \geq 0$, $a > 0$ and $b > 0$.

According to exemplary embodiments, in a method of preparing a cathode active material for a lithium secondary battery, a lithium metal oxide particle is prepared. The lithium metal oxide particle is cleaned using a washing solution that includes a thio-based compound, the thio-based compound having a double bond that contains a sulfur atom.

In some embodiments, an adding amount of the thio-based compound may be in a range from 0.05 weight percent to 2 weight percent based on a total weight of the lithium metal oxide particle.

In some embodiments, an adding amount of the thio-based compound may be in a range from 0.1 weight percent to 1 weight percent based on a total weight of the lithium metal oxide particle.

In some embodiments, before cleaning the lithium metal oxide particle, the lithium metal oxide particle may be mixed and annealed with at least one of $Al_2O_3$, $ZrO_2$ or $TiO_2$.

In some embodiments, the thio-based compound may include at least one selected from a group consisting of a thioamide compound, a tri-thiocarbonate compound and a thiosulfate compound.

In some embodiments, the washing solution may include the thiosulfate compound, and the thiosulfate compound includes a thiosulfate anion ($S_2O_3^{2-}$) salt containing an alkali metal or an alkali earth metal.

In some embodiments, cleaning the lithium metal oxide particle may include a first washing treatment and a second washing treatment, and an active material cake is formed by the first washing treatment.

In some embodiments, the second washing treatment may include providing the washing solution to flow through the active material cake without stirring.

In some embodiments, an amount of the thiosulfate compound in the washing solution used in the first washing treatment may be greater than an amount of the thiosulfate compound in the washing solution used in the second washing treatment.

According to exemplary embodiments, a lithium secondary battery includes a cathode including a lithium metal oxide particle and a thio-based compound formed on at least portion of a surface of the lithium metal oxide particle, the thio-based compound having a double bond that contains a sulfur atom; an anode; and a separation layer interposed between the cathode and the anode.

According to exemplary embodiments of the present invention, a thio-coating may be formed on a surface of a lithium metal oxide particle so that a side reaction with an electrolyte may be prevented while maintaining stability of a layer structure in the lithium metal oxide particle. In some embodiments, when the layer structure of the lithium metal oxide particle is damaged, a metal ion complex may be formed by the thio-coating. Thus, structural and crystalline stability may be enhanced by the thio-coating, and thus stability and capacity/power retention of a cathode active material may be also improved.

In exemplary embodiments, the thio-coating may be introduced from a washing process using a washing solution that may include a thio-amide compound, a tri-thio carbonate compound and/or a thio-sulfate compound. Accordingly, impurities such as lithium salt precipitates remaining on the surface of the lithium metal oxide particle may be removed while forming the thio-coating.

DETAILED DESCRIPTION OF THE EMBODIMENTS

Figure 1:
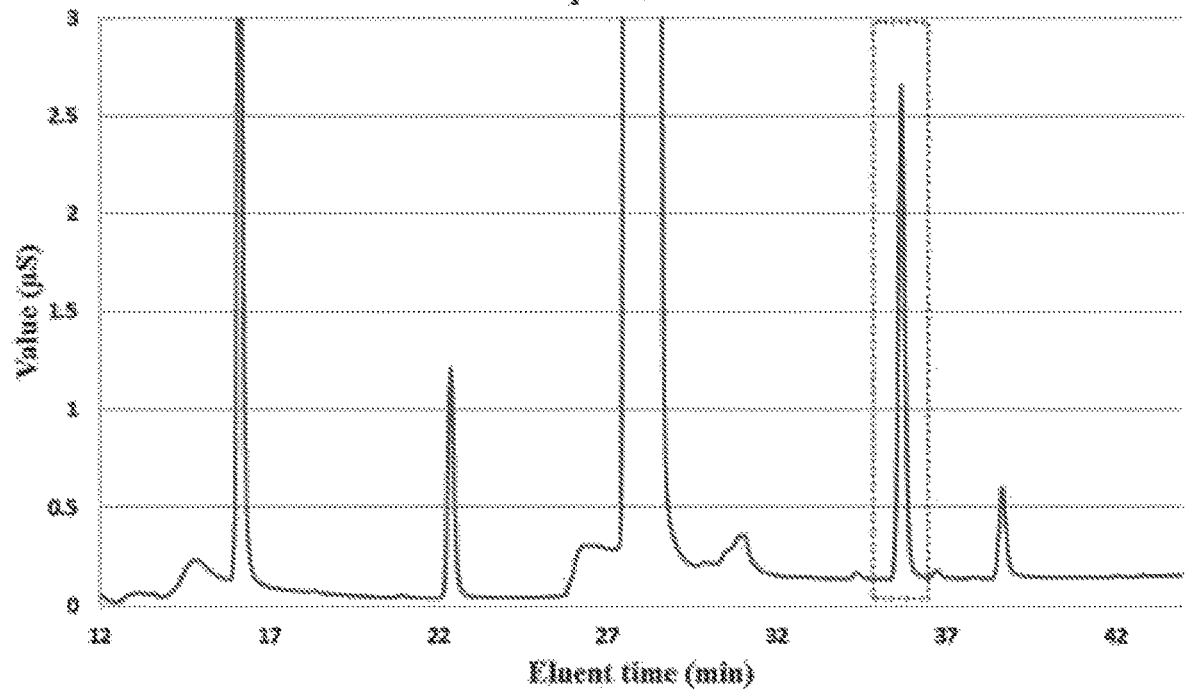
FIG. 1 is a graph showing an ion chromatography analysis result of a cathode active material of Example 10-4.

<Cathode Active Material and Method of Manufacturing the Same>

A cathode active material for a lithium secondary battery (hereinafter, abbreviated as a cathode active material) according to exemplary embodiments may include a lithium metal oxide particle and a thio-based compound formed on a surface of the lithium metal oxide particle.

The term "lithium metal oxide" used herein indicates a complex oxide including lithium and at least one metal except for lithium. In exemplary embodiments, the lithium metal oxide may include a nickel-based lithium oxide.

For example, the nickel-based lithium oxide may be represented by General Formula 1 below.

  [General Formula 1]

In the General Formula 1 above, 0.95≤x≤1.08, y≥0.5, and M may be at least one element selected from Co, Mn, Al, Zr, Ti, B, Mg or Ba.

For example, in the lithium metal oxide of General Formula 1, nickel (Ni) may be an element related to a capacity of a lithium secondary battery. For example, as an amount of nickel becomes greater, a capacity and a power output of the lithium secondary battery may be improved.

In an embodiment. 0.8≤y≤0.93 in General Formula 1 so that a cathode active material providing high capacity and power output may be easily obtained.

M may include cobalt (Co) and manganese (Mn) so that electrical conductivity and chemical stability may be added to a high-Ni compound. For example, cobalt (Co) may be an element related to a conductivity and a resistance of the lithium secondary battery. In an embodiment, M may include manganese (Mn), and Mn may be an element related to mechanical and electrical stability of the lithium secondary battery.

Accordingly, the lithium metal oxide particle may include a nickel-cobalt-manganese based compound, and the cathode active material having improved capacity, power output, low resistance and life-span may be provided.

In some embodiments, the lithium metal oxide particle may further include a doping element or a coating element in addition to Ni, Co and Mn. For example, the doping or coating element may include Al, Zr and/or Ti, and may preferably include Al, Zr and Ti.

In the nickel-cobalt-manganese based lithium oxide, an amount of the doping element may be in a range from about 0.1 mol % to about 1 mol % based on a total mole of Ni, Co, Mn and the doping element (e.g., Al, Zr and/or Ti), preferably in a range from about 0.5 mol % to about 1 mol %. Within the above range, chemical and structural stability of the lithium metal oxide particle may be enhanced without excessively degrading an activity of the cathode active material.

The coating element may be derived from a coating metal oxide such as $Al_2O_3$, $ZrO_2$ and/or $TiO_2$. An adding amount of the coating metal oxide for a formation of the coating may be in a range from about 0.5 wt % to about 1 wt % based on a total weight of the nickel-cobalt-manganese based lithium oxide.

In some embodiments, the lithium metal oxide particle may have a layer structure. For example, primary particles of the lithium metal oxide may be agglomerated into the layer structure to form the lithium metal oxide particle as the cathode active material. A mobility of lithium ions generated from the cathode active material may be facilitated through the particle structure.

In some embodiments, the thio-based compound may be formed on the surface of the lithium metal oxide particle as a thio-coating.

The term "thio-coating" used herein may include a coating layer formed on a substantially entire surface of the lithium metal oxide particle, and a coating layer or an island-shape layer formed on a portion of the surface of the lithium metal oxide particle.

In some embodiments, the thio-coating may include an organic ligand bond attached on the surface of the lithium metal oxide particle, or an organic-metal complex combined with a metal ion exposed on surface of the lithium metal oxide particle.

In some embodiments, a grain boundary at a surface portion of the lithium metal oxide particle may be coated by the thio-coating.

The thio-coating may be derived from a compound including a double bond that contains a sulfur atom (e.g., S=S or S=C). In exemplary embodiments, the thio-coating may be derived from t least one of a thioamide compound, a tri-thiocarbonate compound or a thiosulfate compound.

In the present specification, the thioamide compound may also indicate a thioamide salt.

In some embodiments, the thioamide compound may include a compound represented by Structural Formula 1 below.

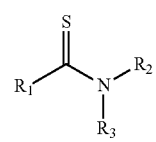  [Structural Formula 1]

In the structural Formula 1 above, $R_1$ may represent hydrogen, halogen, a salt containing $O^-$ or $S^-$, a C1-C10 hydrocarbon group capable of substituted with a substituent group, a C1-C10 alkoxy group, an amine group, an amine group substituted with a C1-C10 alkyl group, a C1-C10 thioalkyl group or a thioamide group.

The term "hydrocarbon group" used herein may include a cyclic aliphatic group, a linear aliphatic group, an aromatic group or a combination thereof. For example, the hydrocarbon group may include an alkyl group, an alkenyl group (e.g., C2-C10), an aryl group (e.g., C6-C10), an aryl alkyl group (e.g., C7-C10), a cyclo alkyl group (e.g., C3-C10) or a multi-cyclic group (e.g., C5-C10). The substituent group capable of being combined with the hydrocarbon group may include, e.g., halogen, a cyano group, a hydroxyl group, a carboxyl group, etc.

The hydrocarbon group included in $R_1$ may be substituted or connected by at least one selected from a group consisting of a carbon-carbon double bond, —O—, —S—, —CO—, —OCO—, —SO—, —CO—O—, —O—CO—O—, —S—CO—, —S—CO—O—, —CO—NH—, —NH—CO—O—, —NR'—, >P=O, —S—S— and —SO$_2$—. R' may be hydrogen or a C1-C8 alkyl group.

The salt containing $O^-$ or $S^-$ included in $R_1$ may be a salt or an ionic bond structure between $O^-$ or $S^-$, and an alkaline metal cation/an alkaline earth metal cation (e.g., $Li^+$, $Na^+$, $K^+$, $Cs^+Ca^{2+}$, $Mg^{2+}$), $N^+R_4$ or $P^+R_4$, and $R_4$ may be hydrogen or a C1-C8 alkyl group.

In the structural Formula 1 above, $R_2$ and $R_3$ may each independently represent hydrogen or a C1-C10 hydrocarbon group capable of substituted with a substituent group. The hydrocarbon group included in $R_2$ and $R_3$ may include an alkyl group, an alkenyl group (e.g., C2-C10), an aryl group (e.g., C6-C10), an aryl alkyl group (e.g., C7-C10), a cyclo alkyl group (e.g., C3-C10) or a multi-cyclic group (e.g., C5-C10). The substituent group capable of being combined with the hydrocarbon group may include, e.g., halogen, a cyano group, a hydroxyl group, a carboxyl group, etc.

The hydrocarbon group included in $R_2$ and $R_3$ may be substituted or connected by at least one selected from a group consisting of a carbon-carbon double bond, —O—, —S—, —CO—, —OCO—, —SO—, —CO—O—, —O—CO—O—, —S—CO—, —S—CO—O—, —CO—NH—, —NH—CO—O—, —NR"—, >P=O, —S—S— and —SO$_2$—. R" may be hydrogen or a C1-C8 alkyl group.

In some embodiments, $R_2$ and $R_3$ may be fused together to form a ring. For example, $R_2$ and $R_3$ may be fused together to form a hetero-ring (e.g., a cyclic ether).

In some embodiments, the thioamide compound may include at least one of compounds represented by Chemical Formula 1 (thiosemicarbazide), Chemical Formula. 2 (thiourea), Chemical Formula 3 (O-ethyl carbamothioate), Chemical Formula 4 (thioacetamide), Chemical Formula 5 (dithiooxamide), Chemical Formula 6 (dimethylcarbamothioic chloride), Chemical Formula 7 (N,N-dimethylmethanethioamide), Chemical Formula 8 (Tetramethylthiuram monosulfide), Chemical Formula 9 (Tetramethylthiuram disulfide), Chemical Formula 10 (N,N-dimethylmorpholine-4-carbothioamide), Chemical Formula 11 (N-cyclohexylmorpholine-4-carbothioamide), Chemical Formula 12 (((ethylthio)carbonothioyl)glycine), Chemical Formula 13 (2-(4-oxo-2-thioxothiazolidin-3-yl)acetic acid), or Chemical Formulae 14-19.

[Chemical Formula 1]

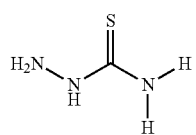

[Chemical Formula 2]

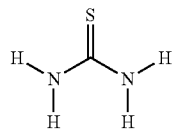

[Chemical Formula 3]

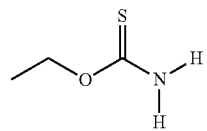

[Chemical Formula 4]

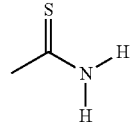

[Chemical Formula 5]

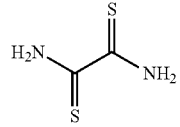

[Chemical Formula 6]

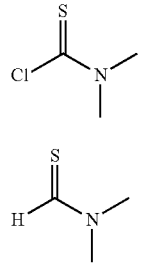

[Chemical Formula 7]

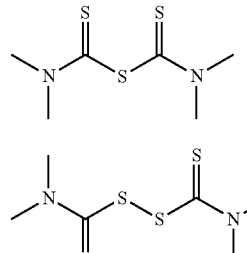

[Chemical Formula 8]

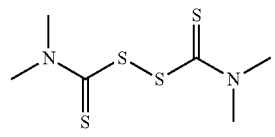

[Chemical Formula 9]

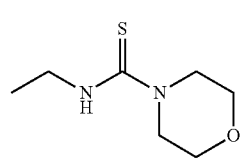

[Chemical Formula 10]

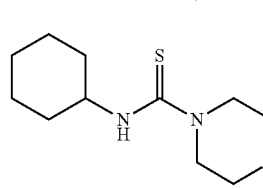

[Chemical Formula 11]

[Chemical Formula 12]

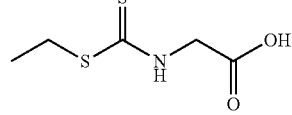

[Chemical Formula 13]

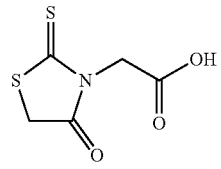

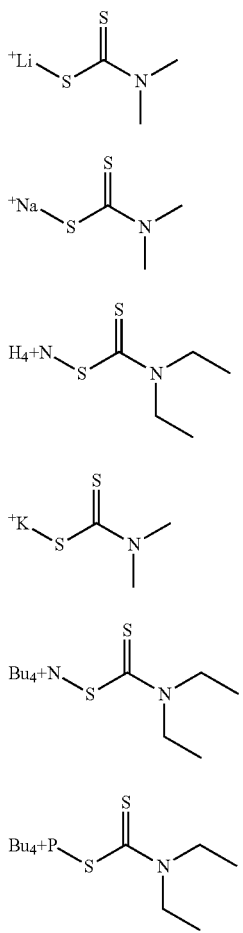

[Chemical Formula 14]

[Chemical Formula 15]

[Chemical Formula 16]

[Chemical Formula 17]

[Chemical Formula 18]

[Chemical Formula 19]

The tri-thiocarbonate compound may include a compound represented by Structural Formula 2 below.

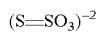

[Structural Formula 2]

In the structural Formula 2 above, $R^1$ and $R^2$ may each independently represent hydrogen or a C1-C10 hydrocarbon group capable of substituted with a substituent group. The hydrocarbon group included in $R^1$ and $R^2$ may include an alkyl group (e.g., C1-C10), an alkenyl group (e.g., C2-C10), an aryl group (e.g., C6-C10), an aryl alkyl group (e.g., C7-C10), a cyclo alkyl group (e.g., C3-C10) or a multi-cyclic group (e.g., C5-C10). The substituent group capable of being combined with the hydrocarbon group may include, e.g., halogen, a cyano group, a hydroxyl group, a carboxyl group, etc.

In some embodiments, $R^1$ and $R^2$ may be fused together to form a ring. For example, $R^1$ and $R^2$ may be fused together to form a hetero-ring.

In some embodiments, the tri-thiocarbonate compound may include at least one of compounds represented by Chemical Formula 20 or 21.

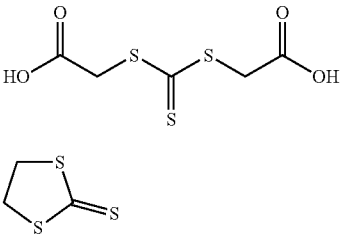

[Chemical Formula 20]

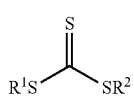

[Chemical Formula 21]

The thiosulfate compound may include a salt containing an ion represented by Structural Formula 3.

$(S=SO_3)^{-2}$ [Structural Formula 3]

For example, the thiosulfate compound may include at least one of salts represented by Chemical Formulae 22 to 24.

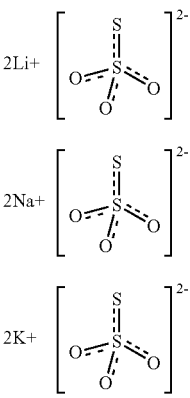

[Chemical Formula 22]

[Chemical Formula 23]

[Chemical Formula 24]

The thio-based compound including the thioamide compound, the tri-thiocarbonate compound or the thiosulfate compound may, e.g., form a coating layer, a ligand bond or a complex on the surface of the lithium metal oxide particle. Thus, the surface of the lithium metal oxide particle may be effectively protected, and the lithium metal oxide particle may be protected from, e.g., a side-reaction with an electrolyte.

Even when a layer structure of the lithium metal oxide particle may be transformed or damaged due to repeated charging/discharging operations, the bond or the complex may be formed with exposed or discharged metal ions by the thio-based compound so that by-products caused by a side-reaction of the metal ions may be prevented or reduced.

Further, if the lithium metal oxide particle includes the additional doping or coating, the thio-based compound may be combined with the doping or coating to further improve chemical stability of the cathode active material.

In some embodiments, the lithium metal oxide particle may include a thiosulfate anion ($S_2O_3^{2-}$) combined with at least a portion of a surface of the lithium metal oxide particle. For example, the thiosulfate anion may be directly bonded to the surface of the lithium metal oxide particle.

Thus, the thiosulfate anion may prevent a lithium-nickel oxide exposed at the surface of the lithium metal oxide particle from being reacted with air or moisture to generate by-products such as lithium hydroxide, lithium carbonate, nickel oxide, etc. Further, phase-transition and transformation of a crystalline structure at a surface portion due to a reaction between nickel ions exposed at the surface and an electrolyte may be suppressed.

In exemplary embodiments, a content of the thiosulfate anion from the lithium metal oxide particle may be measured by an ion chromatography analysis.

In the ion chromatography analysis, an extraction solution may be obtained. In some embodiments, the cathode active material may be input in a $Na_2CO_3$ buffer solution, mixed for 3 hours at room temperature and filtered to obtain the extraction solution.

The extraction solution may be introduced in an ion chromatography apparatus to measure a peak area of the thiosulfate anion. For quantitative analysis, the peak area of the thiosulfate anion formed at the surface of the lithium metal oxide particle may be compared to a peak area of a standard solution, and then the amount of the thiosulfate anion may be calculated by a conversion according to a concentration.

In exemplary embodiments, the content of the thiosulfate anion may be in a range from about 100 ppb to about 8,000 ppb. If the content of the thiosulfate anion is less than about 100 ppb, life-span property of the battery may be deteriorated. If the content of the thiosulfate anion exceeds about 8,000 ppb, a discharge capacity and an initial efficiency of the battery may be excessively degraded. Preferably, the content of the thiosulfate anion may be in a range from about 400 ppb to about 5,000 ppb. More preferably, the content of the thiosulfate anion may be in a range from about 400 ppb to about 2,000 ppb. Within the above range, structural stability of the surface of the lithium metal oxide particle may be enhanced, and lithium impurities may be sufficiently removed.

In some embodiments, a surface component represented by General Formula 2 may be detected by a Time of Flight Secondary Ion Mass Spectrometry (TOF-SIMS) analysis on the surface of the lithium metal oxide particle.

$$M1_x C_y H_z S_a O_b \qquad \text{[General Formula 2]}$$

In General Formula 2, M1 may represent an alkali metal or an alkali earth metal. Here, x≥0, y≥0, z≥0, a>0 and b>0.

In some embodiments, M1 may include a metal ion of sodium, calcium, potassium, barium, etc. M1 may be selected according to a type of the thiosulfate compound in a washing solution used in a cleaning process. For example, the surface component including $NaSO_6^-$ and $C_5H_5S_3O_3^-$ may be detected. It is confirmed or predicted that the thiosulfate anion is combined with the surface of the lithium metal oxide through the detection of the surface component.

Hereinafter, a method of preparing the cathode active material will be described in more detail.

In exemplary embodiments, a lithium precursor and a nickel precursor may be reacted with each other to form the lithium metal oxide particle. The lithium precursor and the nickel precursor may include an oxide or a hydroxide of lithium and nickel, respectively. For example, the lithium precursor and the nickel precursor may be reacted in a solution by a precipitation reaction such as a co-precipitation to form a preliminary lithium metal oxide.

In some embodiments, another metal precursor (e.g., a cobalt precursor, a manganese precursor, etc.) in addition to the lithium precursor and the nickel precursor may be also reacted. In some embodiments, a nickel-cobalt-manganese precursor (e.g., a Ni—Co—Mn hydroxide) may be used together with the lithium precursor.

Another metal precursor may include a precursor of Al, Zr and/or Ti in addition to the cobalt precursor and the manganese precursor in consideration of forming the doping.

In some embodiments, after preparing the preliminary lithium metal oxide, a firing process (or a calcination process) may be further performed. For example, the firing process may be performed at a temperature in a range from about 600° C. to about 1,000° C. The layer structure on the lithium metal oxide particle may be stabilized by the firing process and the doping element may be fixed.

In some embodiments, the lithium metal oxide particle may be mixed with a metal oxide for forming a coating such as $Al_2O_3$, $ZrO_2$ and/or $TiO_2$, and then an additional annealing process may be further performed to form a coating.

In exemplary embodiments, the lithium metal oxide particle may be washed or cleaned using a washing solution that contains the thio-based compound as described above.

Non-reacted precursors may be remained or precipitated on a surface of the lithium metal oxide particle synthesized by the precursor reaction as described above. Further, impurities and solution molecules may be remained on the lithium metal oxide particle during the synthesis.

In some embodiments, an excess amount of the lithium precursor may be used for a production efficiency of the lithium metal oxide particle and a synthesis stability. In this case, lithium salt impurities including, e.g., lithium hydroxide (LiOH) and lithium carbonate ($Li_2CO_3$) may be remained on the surface of the lithium metal oxide particle.

The lithium salt impurities may be captured and removed by the thio-based compound included in the washing solution. In a comparative example, when water is used in the washing solution, the lithium salt impurities may be also removed. However, an oxidation of the surface the lithium metal oxide particle and a side reaction by water may occur to cause damages of the layer structure in the cathode active material. Further, the layer structure may be transformed into a spinel structure and/or a halite structure by water to cause a hydrolysis of a lithium-nickel based oxide and generate nickel impurities such as NiO or $Ni(OH)_2$.

However, according to exemplary embodiments, the washing process may be performed using the washing solution that includes the thio-based compound so that the lithium salt impurities may be effectively removed through a bond formation between the thio-based compound and a metal while preventing the oxidation and the layer structure damages of the particle surface by water.

Additionally, the thio-coating may be formed as described above during the washing process so that removal of the impurities and passivation of the particle surface may be simultaneously implemented.

In some embodiments, an amount of the thio-based compound may be in a range from about 0.05 wt % to about 2 wt % based on a total weight of the lithium metal oxide particle. Within this range, sufficient coating and passivation may be achieved without an excessive degrading activity of the metal included in the cathode active material.

Preferably, the amount of the thio-based compound may be in a range from about 0.1 wt % to about 1 wt % based on the total weight of the lithium metal oxide particle.

In some embodiments, the washing solution may be prepared by dissolving the thio-based compound in water. In an embodiment, an organic solvent such as an alcohol-based solvent may be used in the washing solution.

In some embodiments, when the thiosulfate salt is used as the thio-based compound, other alkaline metal salts such as NaOH or $NaBH_4$ may be excluded in the washing solution.

In some embodiments, a drying process may be further performed after the washing process. The thio-coating may be fixed or stabilized on the particle surface by the drying process.

In some embodiments, a thiosulfate anion ($S_2O_3^{2-}$) may be combined with at least a portion of the surface of the lithium metal oxide particle using the washing solution including the thiosulfate compound.

In some embodiments, at least two washing treatments may be performed. For example, a first washing treatment and a second washing treatment may be sequentially performed. In the first washing treatment, the washing solution may be supplied to the lithium metal oxide particle, and filtered to form an active material cake having a dough shape. The active material cake may have a porous structure in which the lithium metal oxide particles may be physically aggregated to form flow paths.

In the second washing treatment, the washing solution may be input over the active material cake without stirring to penetrate pores or the flow paths formed therein. Thus, the washing or cleaning process may be easily performed without additionally stirring or mixing the lithium metal oxide particles with the washing solution.

The washing solution may be prepared by dissolving the thiosulfate compound in a washing solvent. The thiosulfate compound may include a thiosulfate ($S_2O_3^{2-}$) salt containing an alkali metal or an alkali earth metal. For example, sodium thiosulfate, calcium thiosulfate, potassium thiosulfate and/or barium thiosulfate may be used as the thiosulfate compound. The thiosulfate compound may be easily dissolved in water so that the washing solution may be easily prepared at room temperature while preventing precipitation of the thiosulfate compound.

In some embodiments, an amount of the thiosulfate compound may be in a range from about 0.01 wt % to about 2 wt % based on a total weight of the washing solution. Within this range, the thiosulfate anion may be combined with the surface of the lithium metal oxide particle by the above-mentioned amount through the washing process. Preferably, the amount of the thiosulfate compound may be in a range from 0.1 wt % to about 2 wt % based on a total weight of the washing solution.

If the amount of the thiosulfate compound exceeds about 2 wt %, an excessive amount of the thiosulfate anion may be combined with the surface of the lithium metal oxide particle to degrade an initial discharging amount and an initial efficiency of the cathode active material.

In some embodiments, an amount of the thiosulfate compound in the washing solution for the first washing treatment (a first washing solution) may be greater than that in the washing solution for the second washing treatment (a second washing solution). The active material cake having the thiosulfate anion bonded to a surface thereof may be formed using the first washing solution. The second washing solution may include a relatively large amount of the washing solvent so that impurities remaining on the surface of the lithium metal oxide particle may be effectively removed.

Drying and/or annealing processes may be performed after the washing treatments using the washing solution. For example, the lithium metal oxide particle may be thermally treated in a vacuum atmosphere for a predetermined time after the washing treatment.

The annealing process may be performed at a temperature, e.g., in a range from about 200° C. to about 300° C. For example, the annealing temperature may be slowly increased to a target temperature at a rate of about 1-5° C./min. The lithium metal oxide particle may be maintained in a furnace at the target temperature for a predetermined time. Accordingly, the lithium metal oxide particle to which the thiosulfate anion is fixed may be achieved.

The thermally treated lithium metal oxide particle may be distributed using a mesh of a predetermined pore size to serve as the cathode active material.

<Lithium Secondary Battery>

According to exemplary embodiments, a lithium secondary battery may include a cathode including the lithium metal oxide particle on which the thio-coating may be formed, an anode and a separation layer.

The cathode may include a cathode active material layer formed by coating a cathode active material that may include the lithium metal oxide particle on a cathode current collector.

For example, the lithium metal oxide particle may be mixed and stirred together with a binder, a conductive agent and/or a dispersive agent in a solvent to form a slurry. The slurry may be coated on the cathode current collector, and pressed and dried to obtain the cathode.

The cathode current collector may include stainless-steel, nickel, aluminum, titanium, copper or an alloy thereof. Preferably, aluminum or an alloy thereof may be used.

The binder may include an organic based binder such as a polyvinylidene fluoride-hexafluoropropylene copolymer (PVDF-co-HFP), polyvinylidenefluoride (PVDF), polyacrylonitrile, polymethylmethacrylate, etc., or an aqueous based binder such as styrene-butadiene rubber (SBR) that may be used with a thickener such as carboxymethyl cellulose (CMC).

For example, a PVDF-based binder may be used as a cathode binder. In this case, an amount of the binder for forming the cathode active material layer may be reduced, and an amount of the cathode active material may be relatively increased. Thus, capacity and power output of the lithium secondary battery may be further improved.

The conductive agent may be added to facilitate an electron mobility between the active material particles. For example, the conductive additive may include a carbon-based material such as graphite, carbon black, graphene, carbon nanotube, etc., and/or a metal-based material such as tin, tin oxide, titanium oxide, a perovskite material such as $LaSrCoO_3$ or $LaSrMnO_3$.

The anode may include an anode current collector and an anode active material layer formed by coating an anode active material on the anode current collector.

The anode active material may include a material that may be capable of adsorbing and ejecting lithium ions. For example, a carbon-based material such as a crystalline carbon, an amorphous carbon, a carbon complex or a carbon fiber, a lithium alloy, silicon, tin, etc., may be used. The amorphous carbon may include a hard carbon, cokes, a mesocarbon microbead (MCMB) calcinated at a temperature of 1,500° C. or less, a mesophase pitch-based carbon fiber (MPCF), etc. The crystalline carbon may include a graphite-based material such as natural graphite, graphitized cokes, graphitized MCMB, graphitized MPCF, etc. The lithium alloy may further include aluminum, zinc, bismuth, cadmium, antimony, silicon, lead, tin, gallium, or indium.

The anode current collector may include gold, stainless-steel, nickel, aluminum, titanium, copper or an alloy thereof, preferably, may include copper or a copper alloy.

In some embodiments, the anode active material may be mixed and stirred together with a binder, a conductive agent and/or a dispersive agent in a solvent to form a slurry. The slurry may be coated on the anode current collector, and pressed and dried to obtain the anode.

The binder and the conductive agent substantially the same as or similar to those as mentioned above may be used. In some embodiments, the binder for the anode may include an aqueous binder such as such as styrene-butadiene rubber (SBR) that may be used with a thickener such as carboxymethyl cellulose (CMC) so that compatibility with the carbon-based active material may be improved.

The separation layer may be interposed between the cathode and the anode. The separation layer may include a porous polymer film prepared from, e.g., a polyolefin-based polymer such as an ethylene homopolymer, a propylene homopolymer, an ethylene/butene copolymer, an ethylene/hexene copolymer, an ethylene/methacrylate copolymer, or the like. The separation layer may be also formed from a non-woven fabric including a glass fiber with a high melting point, a polyethylene terephthalate fiber, or the like.

In exemplary embodiments, an electrode cell may be defined by the cathode, the anode and the separation layer, and a plurality of the electrode cells may be stacked to form an electrode assembly having, e.g., a jelly roll shape. For example, the electrode assembly may be formed by winding, laminating or folding of the separation layer.

The electrode assembly may be accommodated in an outer case together with an electrolyte to form the lithium secondary battery. In example embodiments, the electrolyte may include a non-aqueous electrolyte solution.

The non-aqueous electrolyte solution may include a lithium salt and an organic solvent. The lithium salt may be represented by $Li^+X^-$, and an anion of the lithium salt $X^-$ may include, $F^-$, $Cl^-$, $Br^-$, $I^-$, $NO_3^-$, $N(CN)_2^-$, $BF_4^-$, $ClO_4^-$, $PF_6^-$, $(CF_3)_2PF_4^-$, $(CF_3)_3PF_3^-$, $(CF_3)_4PF_2^-$, $(CF_3)_5PF^-$, $(CF_3)_6P^-$, $CF_3SO_3^-$, $CF_3CF_2SO_3^-$, $(CF_3SO_2)_2N^-$, $(FSO_2)_2N^-$, $CF_3CF_2(CF_3)_2CO^-$, $(CF_3SO_2)_2CH^-$, $(SF_5)_3C^-$, $(CF_3SO_2)_3C^-$, $CF_3(CF_2)_7SO_3^-$, $CF_3CO_2^-$, $CH_3CO_2^-$, $SCN^-$, $(CF_3CF_2SO_2)_2N^-$, etc.

The organic solvent may include propylene carbonate (PC), ethylene carbonate (EC), diethyl carbonate (DEC), dimethyl carbonate (DMC), ethylmethyl carbonate (EMC), methylpropyl carbonate, dipropyl carbonate, dimethyl sulfoxide, acetonitrile, dimethoxy ethane, diethoxy ethane, vinylene carbonate, sulfolane, gamma-butyrolactone, propylene sulfite, tetrahydrofuran, etc. These may be used alone or in a combination thereof.

An electrode tab may be formed from each of the cathode current collector and the anode current collector to extend to one end of the outer case. The electrode tabs may be welded together with the one end of the outer case to form an electrode lead exposed at an outside of the outer case.

The lithium secondary battery may be fabricated into a cylindrical shape using a can, a prismatic shape, a pouch shape, a coin shape, etc.

According to exemplary embodiments, chemical stability of the cathode active material may be enhanced by the thio-coating so that life-span and long-term stability of the lithium secondary battery may be improved while suppressing a reduction of a capacity and an average voltage.

Hereinafter, preferred embodiments are proposed to more concretely describe the present invention. However, the following examples are only given for illustrating the present invention and those skilled in the related art will obviously understand that various alterations and modifications are possible within the scope and spirit of the present invention. Such alterations and modifications are duly included in the appended claims.

Experimental Example 1

Examples and Comparative Examples

In Examples and Comparative Examples, lithium metal oxides having a composition as shown in Table 1 below ($Li[Ni_{0.88}Co_{0.09}Mn_{0.03}]O_2$ or $Li[Ni_{0.8}Co_{0.1}Mn_{0.1}]O_2$) or lithium metal oxides including a clopping of Al, Zr and Ti or a coating of $Al_2O_3$, $ZrO_2$ and $TiO_2$ were used. De-ionized water (DIW) having a resistivity less than 25MΩcm was used in a washing process.

Examples 1 kg of pure water (DIW) was put in a 2 L reactor, and dissolved oxygen in pure water was sufficiently removed by a nitrogen bubbling for 30 minutes. Then, a thio-based compound as listed in Table 1 was input by an amount as stated in Table 1 based on a weight of the lithium metal oxide and stirred for 30 minutes. 1 kg of the lithium metal oxide of Table 1 as a cathode active material was further input, stirred for 30 minutes at a speed of 300 rpm in a nitrogen atmosphere, and then vacuum filtrated using Buchner funnel. The filtrated lithium metal oxide was dried at a temperature of 200° C. to 300° C. for 24 hours, and distributed using 325 mesh to obtain a desired lithium metal oxide.

Comparative Examples

Processes substantially the same as or similar to those of Examples were performed except that a pure water was used as a washing solution and the thio-based compound was not used.

TABLE 1

| | Cathode Active Material | Doping amount (mol %) | | | Coating Amount (wt %) | | | Added Compound | wt % |
|---|---|---|---|---|---|---|---|---|---|
| | | Al | Zr | Ti | $Al_2O_3$ | $ZrO_2$ | $TiO_2$ | | |
| Example 1-1 | $Li[Ni_{0.88}Co_{0.09}Mn_{0.03}]O_2$ | | | | | | | Dithiooxamide | 0.5 |
| Example 1-2 | $Li[Ni_{0.88}Co_{0.09}Mn_{0.03}]O_2$ | | | | | | | Sodium Dimethyldithiocarbamate Dihydrate | 0.5 |
| Example 1-3 | $Li[Ni_{0.88}Co_{0.09}Mn_{0.03}]O_2$ | | | | | | | sodium 2-Thiobarbiturate | 0.5 |
| Example 1-4 | $Li[Ni_{0.88}Co_{0.09}Mn_{0.03}]O_2$ | | | | | | | thiosemicarbazide | 0.5 |
| Example 1-5 | $Li[Ni_{0.88}Co_{0.09}Mn_{0.03}]O_2$ | | | | | | | thioacetamide | 0.5 |
| Example 1-6 | $Li[Ni_{0.88}Co_{0.09}Mn_{0.03}]O_2$ | | | | | | | N,N bis(carboxymethyl) dithiooxamide | 0.5 |
| Example 1-7 | $Li[Ni_{0.88}Co_{0.09}Mn_{0.03}]O_2$ | | | | | | | Bis(carboxymethyl) trithiocarbonate | 0.5 |

TABLE 1-continued

| | Cathode Active Material | Doping amount (mol %) | | | Coating Amount (wt %) | | | Added Compound | wt % |
|---|---|---|---|---|---|---|---|---|---|
| | | Al | Zr | Ti | $Al_2O_3$ | $ZrO_2$ | $TiO_2$ | | |
| Example 1-8 | $Li[Ni_{0.88}Co_{0.09}Mn_{0.03}]O_2$ | | | | | | | sodium thiosulfate | 0.5 |
| Example 2-1 | $Li[Ni_{0.88}Co_{0.09}Mn_{0.03}]O_2$ | 0.3 | 0.2 | 0.2 | | | | Dithiooxamide | 0.5 |
| Example 2-2 | $Li[Ni_{0.88}Co_{0.09}Mn_{0.03}]O_2$ | 0.3 | 0.2 | 0.2 | | | | Sodium Dimethyldithiocarbanate Dihydrate | 0.5 |
| Example 2-3 | $Li[Ni_{0.88}Co_{0.09}Mn_{0.03}]O_2$ | 0.3 | 0.2 | 0.2 | | | | Bis(carboxymethyl) trithiocarbonate | 0.5 |
| Example 2-4 | $Li[Ni_{0.88}Co_{0.09}Mn_{0.03}]O_2$ | 0.3 | 0.2 | 0.2 | | | | sodium thiosulfate | 0.5 |
| Example 3-1 | $Li[Ni_{0.88}Co_{0.09}Mn_{0.03}]O_2$ | | | | 0.5 | 0.06 | 0.2 | Dithiooxamide | 0.5 |
| Example 3-2 | $Li[Ni_{0.88}Co_{0.09}Mn_{0.03}]O_2$ | | | | 0.5 | 0.06 | 0.2 | Sodium Dimethyldithiocarbanate Dihydrate | 0.5 |
| Example 3-3 | $Li[Ni_{0.88}Co_{0.09}Mn_{0.03}]O_2$ | | | | 0.5 | 0.06 | 0.2 | Bis(carboxymethyl) trithiocarbonate | 0.5 |
| Example 3-4 | $Li[Ni_{0.88}Co_{0.09}Mn_{0.03}]O_2$ | | | | 0.5 | 0.06 | 0.2 | sodium thiosulfate | 0.5 |
| Example 4-1 | $Li[Ni_{0.88}Co_{0.09}Mn_{0.03}]O_2$ | | | | 0.5 | 0.06 | 0.2 | Sodium Dimethyldithiocarbanate Dihydrate | 2.0 |
| Example 4-2 | $Li[Ni_{0.88}Co_{0.09}Mn_{0.03}]O_2$ | | | | 0.5 | 0.06 | 0.2 | Sodium Dimethyldithiocarbanate Dihydrate | 1.0 |
| Example 4-3 | $Li[Ni_{0.88}Co_{0.09}Mn_{0.03}]O_2$ | | | | 0.5 | 0.06 | 0.2 | Sodium Dimethyldithiocarbanate Dihydrate | 0.25 |
| Example 4-4 | $Li[Ni_{0.88}Co_{0.09}Mn_{0.03}]O_2$ | | | | 0.5 | 0.06 | 0.2 | Sodium Dimethyldithiocarbanate Dihydrate | 0.10 |
| Example 4-5 | $Li[Ni_{0.88}Co_{0.09}Mn_{0.03}]O_2$ | | | | 0.5 | 0.06 | 0.2 | Sodium Dimethyldithiocarbanate Dihydrate | 0.05 |
| Example 5-1 | $Li[Ni_{0.8}Co_{0.1}Mn_{0.1}]O_2$ | | | | | | | Dithiooxamide | 0.5 |
| Example 5-2 | $Li[Ni_{0.8}Co_{0.1}Mn_{0.1}]O_2$ | | | | | | | Sodium Dimethyldithiocarbanate Dihydrate | 0.5 |
| Example 5-3 | $Li[Ni_{0.8}Co_{0.1}Mn_{0.1}]O_2$ | | | | | | | Bis(carboxymethyl) trithiocarbonate | 0.5 |
| Example 5-4 | $Li[Ni_{0.8}Co_{0.1}Mn_{0.1}]O_2$ | | | | | | | sodium thiosulfate | 0.5 |
| Example 6-1 | $Li[Ni_{0.8}Co_{0.1}Mn_{0.1}]O_2$ | 0.3 | 0.2 | 0.2 | | | | Dithiooxamide | 0.5 |
| Example 6-2 | $Li[Ni_{0.8}Co_{0.1}Mn_{0.1}]O_2$ | 0.3 | 0.2 | 0.2 | | | | Sodium Dimethyldithiocarbanate Dihydrate | 0.5 |
| Example 6-3 | $Li[Ni_{0.8}Co_{0.1}Mn_{0.1}]O_2$ | 0.3 | 0.2 | 0.2 | | | | Bis(carboxymethyl) trithiocarbonate | 0.5 |
| Example 6-4 | $Li[Ni_{0.8}Co_{0.1}Mn_{0.1}]O_2$ | 0.3 | 0.2 | 0.2 | | | | sodium thiosulfate | 0.5 |
| Example 7-1 | $Li[Ni_{0.8}Co_{0.1}Mn_{0.1}]O_2$ | | | | 0.5 | 0.06 | 0.2 | Dithiooxamide | 0.5 |
| Example 7-2 | $Li[Ni_{0.8}Co_{0.1}Mn_{0.1}]O_2$ | | | | 0.5 | 0.06 | 0.2 | Sodium Dimethyldithiocarbanate Dihydrate | 0.5 |
| Example 7-3 | $Li[Ni_{0.8}Co_{0.1}Mn_{0.1}]O_2$ | | | | 0.5 | 0.06 | 0.2 | Bis(carboxymethyl) trithiocarbonate | 0.5 |
| Example 7-4 | $Li[Ni_{0.8}Co_{0.1}Mn_{0.1}]O_2$ | | | | 0.5 | 0.06 | 0.2 | sodium thiosulfate | 0.5 |
| Example 8-1 | $Li[Ni_{0.8}Co_{0.1}Mn_{0.1}]O_2$ | | | | 0.5 | 0.06 | 0.2 | Bis(carboxymethyl) trithiocarbonate | 1.0 |
| Example 8-2 | $Li[Ni_{0.8}Co_{0.1}Mn_{0.1}]O_2$ | | | | 0.5 | 0.06 | 0.2 | Bis(carboxymethyl) trithiocarbonate | 0.25 |
| Example 8-3 | $Li[Ni_{0.8}Co_{0.1}Mn_{0.1}]O_2$ | | | | 0.5 | 0.06 | 0.2 | Bis(carboxymethyl) trithiocarbonate | 0.10 |
| Example 8-4 | $Li[Ni_{0.8}Co_{0.1}Mn_{0.1}]O_2$ | | | | 0.5 | 0.06 | 0.2 | Bis(carboxymethyl) trithiocarbonate | 0.05 |
| Example 9-1 | $Li[Ni_{0.8}Co_{0.1}Mn_{0.1}]O_2$ | | | | 0.5 | 0.06 | 0.2 | sodium thiosulfate | 1.0 |
| Example 9-2 | $Li[Ni_{0.8}Co_{0.1}Mn_{0.1}]O_2$ | | | | 0.5 | 0.06 | 0.2 | sodium thiosulfate | 0.25 |
| Example 9-3 | $Li[Ni_{0.8}Co_{0.1}Mn_{0.1}]O_2$ | | | | 0.5 | 0.06 | 0.2 | sodium thiosulfate | 0.10 |
| Example 9-4 | $Li[Ni_{0.8}Co_{0.1}Mn_{0.1}]O_2$ | | | | 0.5 | 0.06 | 0.2 | sodium thiosulfate | 0.05 |
| Comparative Example 1 | $Li[Ni_{0.88}Co_{0.09}Mn_{0.03}]O_2$ | | | | | | | none | 0.0 |
| Comparative Example 2 | $Li[Ni_{0.88}Co_{0.09}Mn_{0.03}]O_2$ | 0.3 | 0.2 | 0.2 | | | | none | 0.0 |
| Comparative Example 3 | $Li[Ni_{0.88}Co_{0.09}Mn_{0.03}]O_2$ | | | | 0.5 | 0.06 | 0.2 | none | 0.0 |
| Comparative Example 4 | $Li[Ni_{0.8}Co_{0.1}Mn_{0.01}]O_2$ | | | | | | | none | 0.0 |
| Comparative Example 5 | $Li[Ni_{0.8}Co_{0.1}Mn_{0.01}]O_2$ | 0.3 | 0.2 | 0.2 | | | | none | 0.0 |

TABLE 1-continued

| Cathode Active | | Doping amount (mol %) | | | Coating Amount (wt %) | | | | |
|---|---|---|---|---|---|---|---|---|---|
| | Material | Al | Zr | Ti | $Al_2O_3$ | $ZrO_2$ | $TiO_2$ | Added Compound | wt % |
| Comparative Example 6 | $Li[Ni_{0.8}Co_{0.1}Mn_{0.01}]O_2$ | | | | 0.5 | 0.06 | 0.2 | none | 0.0 |

(1) Measurement of Remaining Lithium Salt Impurities 5.0 g of each lithium metal oxide particle according to Examples and Comparative Examples was quantified in a 250 mL flask with 100 g of deionized water, and then a magnetic bar was put and stirred for 10 minutes at a rate of 4 rpm. The mixture was filtered using a pressure reducing flask and 50 g of the mixture was collected. The collected mixture was automatically titrated with 0.1N HCl in an auto titrator to measure amounts of LiOH and $Li_2CO_3$ as shown in Table 2 below.

(2) Evaluation of Battery Properties 2-1) Fabrication of Secondary Battery Cell

Each lithium metal oxide particles of Examples and Comparative Examples, carbon black as a conductive additive and PVDF as a binder were mixed by a weight ratio of 92:5:3 to form a slurry. The slurry was uniformly coated on an aluminum foil having a thickness of 15 μm and vacuum-dried at 130° C. to form a cathode for a lithium secondary battery. An electrode assembly was formed using the cathode, a lithium foil as a counter electrode, a porous polyethylene layer (thickness: 21 μm) as a separator. A battery cell having a coin half cell shape was fabricated by a commonly known process using the electrode assembly and an electrolyte solution in which 1.0 M of LiPF6 was dissolved in a solution including ethylene carbonate and ethyl methyl carbonate by a volume ratio of 3:7.

2-2) Measurement of Initial Charging/Discharging Capacity

One cycle of a charging (CC/CV 0.1 C 4.3V 0.05CA CUT-OFF) and a discharging (CC 0.1 C 3.0V CUT-OFF) was performed to the battery cells of Examples and Comparative Examples, and initial charging and discharging capacities were measured (CC: constant current, CV: Constant voltage)

2-3) Measurement of Initial Efficiency

The initial discharging capacity measured in the above 2-2) was denominated by an initial charging capacity to measure an initial efficiency as a percentage value.

2-4) Measurement of IC Discharging Capacity 300 cycles of a charging (CC/CV 0.5 C 4.3V 005CA CUT-OFF) and a discharging (CC 1.0 C 3.0V CUT-OFF) were repeated using the battery cells of Examples and Comparative Examples. A discharging capacity at the 300th cycle was denominated by the discharging capacity at the first cycle to measure a capacity retention ratio as a percentage value.

The results are shown in Table 2 below.

TABLE 2

| | LiOH wt % | Li2CO3 wt % | Initial Charging Capacity mAh/g | Initial Discharging Capacity mAh/g | Initial Efficiency % | Life-span @300th % |
|---|---|---|---|---|---|---|
| Example 1-1 | 0.156 | 0.185 | 235 | 215 | 91 | 69 |
| Example 1-2 | 0.176 | 0.190 | 235 | 214 | 91 | 71 |
| Example 1-3 | 0.188 | 0.187 | 236 | 214 | 91 | 68 |
| Example 1-4 | 0.153 | 0.179 | 234 | 215 | 92 | 70 |
| Example 1-5 | 0.192 | 0.186 | 238 | 213 | 89 | 68 |
| Example 1-6 | 0.169 | 0.201 | 237 | 215 | 91 | 72 |
| Example 1-7 | 0.174 | 0.190 | 235 | 215 | 91 | 72 |
| Example 1-8 | 0.163 | 0.208 | 236 | 215 | 91 | 71 |
| Example 2-1 | 0.109 | 0.171 | 233 | 215 | 92 | 70 |
| Example 2-2 | 0.099 | 0.199 | 235 | 215 | 91 | 75 |
| Example 2-3 | 0.132 | 0.172 | 234 | 215 | 92 | 72 |
| Example 2-4 | 0.172 | 0.197 | 233 | 214 | 92 | 70 |
| Example 3-1 | 0.145 | 0.144 | 234 | 214 | 91 | 74 |
| Example 3-2 | 0.193 | 0.172 | 236 | 214 | 91 | 76 |
| Example 3-3 | 0.154 | 0.198 | 237 | 214 | 90 | 76 |
| Example 3-4 | 0.176 | 0.186 | 238 | 213 | 89 | 75 |
| Example 4-1 | 0.081 | 0.206 | 233 | 208 | 89 | 69 |
| Example 4-2 | 0.105 | 0.193 | 234 | 210 | 90 | 75 |
| Example 4-3 | 0.181 | 0.168 | 237 | 215 | 91 | 71 |
| Example 4-4 | 0.185 | 0.180 | 240 | 215 | 90 | 70 |
| Example 4-5 | 0.196 | 0.152 | 241 | 216 | 90 | 64 |
| Example 5-1 | 0.195 | 0.131 | 227 | 202 | 89 | 69 |
| Example 5-2 | 0.186 | 0.111 | 226 | 201 | 89 | 73 |
| Example 5-3 | 0.189 | 0.123 | 225 | 201 | 89 | 72 |
| Example 5-4 | 0.192 | 0.112 | 224 | 201 | 90 | 73 |
| Example 6-1 | 0.108 | 0.182 | 224 | 200 | 89 | 71 |
| Example 6-2 | 0.115 | 0.198 | 223 | 201 | 90 | 77 |
| Example 6-3 | 0.157 | 0.178 | 223 | 199 | 89 | 76 |
| Example 6-4 | 0.172 | 0.153 | 223 | 199 | 89 | 77 |
| Example 7-1 | 0.149 | 0.190 | 221 | 200 | 90 | 77 |
| Example 7-2 | 0.173 | 0.183 | 222 | 202 | 91 | 78 |
| Example 7-3 | 0.155 | 0.188 | 225 | 200 | 89 | 79 |
| Example 7-4 | 0.166 | 0.192 | 224 | 199 | 89 | 77 |
| Example 8-1 | 0.170 | 0.198 | 222 | 198 | 89 | 77 |
| Example 8-2 | 0.142 | 0.179 | 225 | 200 | 89 | 79 |
| Example 8-3 | 0.138 | 0.171 | 225 | 199 | 88 | 76 |
| Example 8-4 | 0.139 | 0.178 | 224 | 197 | 88 | 72 |
| Example 9-1 | 0.189 | 0.202 | 222 | 198 | 89 | 76 |
| Example 9-2 | 0.151 | 0.198 | 223 | 199 | 89 | 77 |
| Example 9-3 | 0.138 | 0.204 | 223 | 198 | 89 | 73 |
| Example 9-4 | 0.141 | 0.211 | 224 | 197 | 88 | 71 |
| Comparative Example 1 | 0.121 | 0.192 | 143 | 211 | 87 | 28 |
| Comparative Example 2 | 0.183 | 0.194 | 240 | 208 | 87 | 43 |
| Comparative Example 3 | 0.211 | 0.256 | 240 | 211 | 87 | 45 |
| Comparative Example 4 | 0.111 | 0.198 | 228 | 201 | 88 | 33 |
| Comparative Example 5 | 0.167 | 0.188 | 225 | 197 | 88 | 49 |
| Comparative Example 6 | 0.203 | 0.212 | 223 | 196 | 88 | 50 |

Referring to Table 2 above, when the washing process using the thio-based compound was performed, an amount of lithium impurities was decreased and improved charging/discharging efficiency and capacity retention were obtained.

In Comparative Examples 1 to 6 in which the thio-based compounds were not used, the lithium impurities were not effectively removed, and efficiency and capacity retention were also degraded due to an oxidation of a particle structure.

Experimental Example 2

Fabrication of Cathode Active Material

Lithium metal oxide particles having a composition of Li[Ni$_{0.83}$Co$_{0.11}$Mn$_{0.06}$]O$_2$ were used in Example and Comparative Examples. Thiosulfate additives as listed in Table 3 below and de-ionized water (DIW) having a resistivity of 25MΩcm or less were mixed to prepare thiosulfate washing solutions.

50 g of the lithium metal oxide particle was input in a first washing solution having a concentration as shown in Table 3, stirred for 10 minutes and the vacuum filtrated using Buchner funnel to form an active material cake.

A second washing solution having a concentration as shown in Table 3 was introduced to the active material cake to penetrate through the active material cake without additional stirring and mixing.

The active material cake washed twice using the thiosulfate washing solutions was dried for 10 hours or more at a temperature between 200° C. and 300° C. under a vacuum condition to remove moistures. Subsequently, lithium metal oxide particles as a cathode active material were obtained by a distribution using 325 mesh.

connected with IonPac AS19-4 um Guard Column, and a suppressor was AERS_2 mm. EGC 500 KOH cartridge was used as an eluent and a multi-step gradient analysis was performed. A flow rate of a pump was 0.25 ml/min, a temperature of the column was 30° C., and a pressure in the column was 2900-3200 psi. The analysis was performed for 70 minutes.

More particularly, the multi-step gradient analysis included five steps as follows: First step: 0-5 minutes, KOH 3 mM; Second step: 5-40 minutes, KOH 3-40 mM; Third step: 40-50 minutes, KOH 40 mM, Fourth step: 51-59 minutes, KOH 100 mM; Fifth step: 59.5-70 minutes, KOH 3 mM.

FIG. 1 is a graph showing an ion chromatography analysis result of a cathode active material of Example 10-4. Referring to FIG. 1, a peak of the thiosulfate anion ($S_2O_3^{2-}$) was detected at an eluent time in a range from 35-37 minutes.

Figure 2:
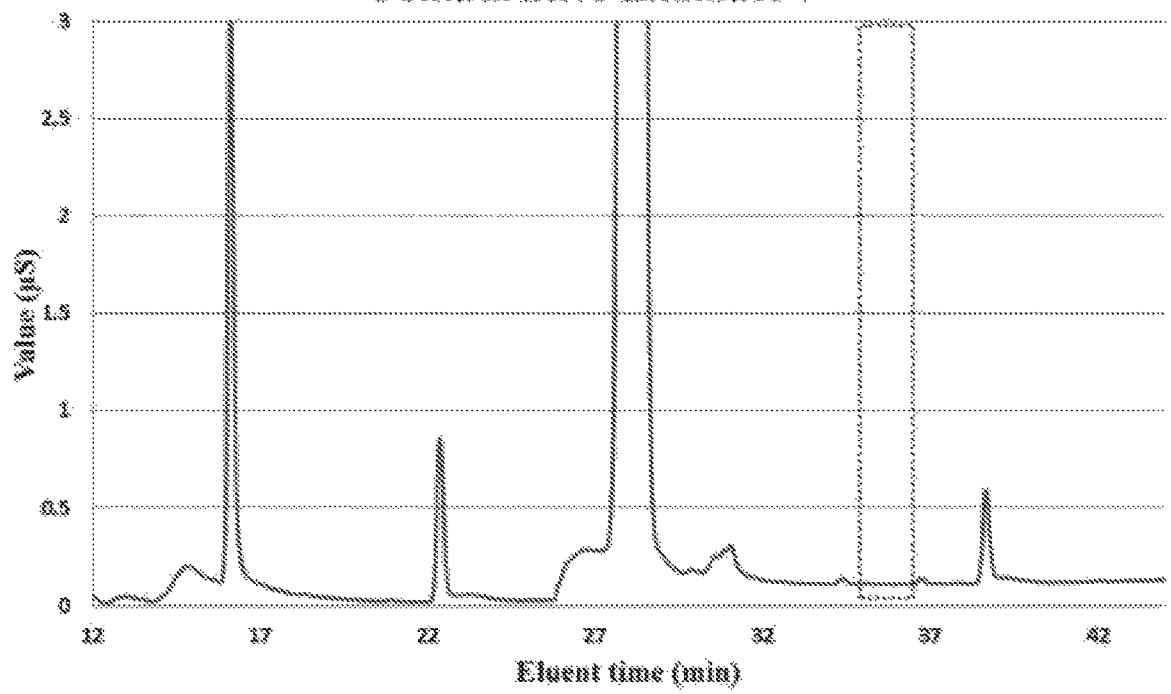
FIG. 2 is a graph showing an ion chromatography analysis result of a cathode active material of Comparative Example 7.

FIG. 2 is a graph showing an ion chromatography analysis result of a cathode active material of Comparative Example 7. Referring to FIG. 2, a peak of the thiosulfate anion ($S_2O_3^{2-}$) was not detected.

For a quantitative calculation, standard solutions, each of which contained the thiosulfate anion by an amount of 60 ppb, 100 ppb, 600 ppb, 1000 ppb, 2000 ppb, and 11000 ppb to perform the IC analysis. A calibration curve relation was induced using a concentration of the standard solution (X,

TABLE 3

| | Cathode Active Material | Thiosulfate Additive | Amount of additive in washing solution (wt %) | |
|---|---|---|---|---|
| | | | First Washing Solution | Second Washing Solution |
| Example 10-1 | Li[Ni$_{0.88}$Co$_{0.09}$Mn$_{0.03}$]O$_2$ | sodium thiosulfate | 0.1 | 0.03 |
| Example 10-2 | Li[Ni$_{0.88}$Co$_{0.09}$Mn$_{0.03}$]O$_2$ | sodium thiosulfate | 0.3 | 0.1 |
| Example 10-3 | Li[Ni$_{0.88}$Co$_{0.09}$Mn$_{0.03}$]O$_2$ | sodium thiosulfate | 0.6 | 0.2 |
| Example 10-4 | Li[Ni$_{0.88}$Co$_{0.09}$Mn$_{0.03}$]O$_2$ | sodium thiosulfate | 1 | 0.33 |
| Example 10-5 | Li[Ni$_{0.88}$Co$_{0.09}$Mn$_{0.03}$]O$_2$ | sodium thiosulfate | 1.5 | 0.5 |
| Example 10-6 | Li[Ni$_{0.88}$Co$_{0.09}$Mn$_{0.03}$]O$_3$ | calcium thiosulfate | 1 | 0.33 |
| Example 10-7 | Li[Ni$_{0.88}$Co$_{0.09}$Mn$_{0.03}$]O$_4$ | potassium thiosulfate | 1 | 0.33 |
| Example 10-8 | Li[Ni$_{0.88}$Co$_{0.09}$Mn$_{0.03}$]O$_5$ | barium thiosulfate | 0.1 | 0.03 |
| Comparative Example 7 | Li[Ni$_{0.88}$Co$_{0.09}$Mn$_{0.03}$]O$_2$ | sodium thiosulfate | 0 | 0 |
| Comparative Example 8 | Li[Ni$_{0.88}$Co$_{0.09}$Mn$_{0.03}$]O$_2$ | sodium thiosulfate | 0.05 | 0.02 |
| Comparative Example 9 | Li[Ni$_{0.88}$Co$_{0.09}$Mn$_{0.03}$]O$_2$ | sodium thiosulfate | 2 | 0.67 |

(1) Analysis of Cathode Active Material

Measurement of Remaining Lithium Salt Impurities

Lithium salt impurities on the lithium metal oxide particles of Examples and Comparative Examples as shown in Table 3 above were measured by the same method as that in Experimental Example 1.

IC Analysis

An ion chromatography (IC) analysis was performed to detect a thiosulfate anion component remaining on surfaces of the cathode active materials of Examples and Comparative Examples. 2 g of each cathode active material was put in 3 mM Na$_2$CO$_3$ buffer solution and mixed for 3 hours at room temperature. The solution was filtered by a 0.2 μm syringe filter, and then introduced to an IC apparatus with an amount of 10 μl for an analysis. A ratio of a sample and an extraction solution (an extraction ratio) was represented by D=extraction solution (g)/active material (g). Specific conditions of the IC analysis were as follows. The IC apparatus was Thermo ICS-6000, a column was IonPac AS19-4 μm ppb) and a peak area (Y, μS/cm·sec) of the thiosulfate anion detected from each standard solution. Specifically, in a low concentration range, the standard solutions of 60 ppb, 100 ppb, 600 ppb and 1000 ppb were used to calculate the calibration curve relation. In a high concentration range, the standard solutions of 2000 ppb and 11000 ppb were used to calculate the calibration curve relation. In the low concentration range, the equation of $Y_1=0.301 X_1-0.006$ was used. In the high concentration range, the equation of $Y_2=0.337X_2-0.048$ was used. A linearity of each calibration curve satisfied the relation of $R^2>0.999$.

In Comparative Example 8, Example 10-1, Example 10-2 and Example 10-3 having relatively low concentrations of the thiosulfate anion, the peak area of the thiosulfate anion was input in $Y_1$ to obtain a content of the thiosulfate anion as $X_1$ in a diluted solution. In Comparative Example 9, Example 10-4 and Example 10-5 having relatively high concentrations of the thiosulfate anion, the peak area of the thiosulfate anion was input in $Y_2$, to obtain the content of the thiosulfate anion as $X_2$ in a diluted solution. Finally, the extraction ratio D was multiplied by each $X_1$ and $X_2$ to obtain a content of the thiosulfate anion.

The results are shown in Table 4 below.

TABLE 4

| | LiOH(ppm) | Li$_2$CO$_3$(ppm) | thiosulphate(S$_2$O$_3{}^{2-}$) content (ppb) |
|---|---|---|---|
| Example 10-1 | 1470 | 1960 | 200 |
| Example 10-2 | 1420 | 2100 | 479 |
| Example 10-3 | 1530 | 2040 | 1990 |
| Example 10-4 | 1680 | 1930 | 4898 |
| Example 10-5 | 1230 | 2140 | 7807 |
| Example 10-6 | 1390 | 2100 | 4703 |
| Example 10-7 | 1420 | 2180 | 4650 |
| Example 10-8 | 1390 | 1990 | 210 |
| Comparative Example 7 | 1410 | 1820 | N.D.(<20 ppb) |
| Comparative Example 8 | 1560 | 1790 | 90 |
| Comparative Example 9 | 1520 | 2000 | 1020 |

(2) Evaluation of Battery Properties

An initial charging/discharging capacity, an initial efficiency and a capacity retention were measured by the same methods as those of Experimental Example 1 The results are shown in Table 5 below.

TABLE 5

| | Initial Charging Capacity mAh/g | Initial Discharging Capacity mAh/g | Initial Efficiency % | Life-span @300th % |
|---|---|---|---|---|
| Example 10-1 | 233.5 | 210.5 | 90.1% | 64% |
| Example 10-2 | 234.0 | 211.0 | 90.2% | 65% |
| Example 10-3 | 233.8 | 210.9 | 90.2% | 67% |
| Example 10-4 | 235.2 | 211.7 | 90.0% | 67% |
| Example 10-5 | 235.4 | 210.7 | 89.5% | 67% |
| Example 10-6 | 235.1 | 211.3 | 89.9% | 65% |
| Example 10-7 | 235.3 | 211.4 | 89.9% | 63% |
| Example 10-8 | 234.4 | 211.3 | 90.1% | 63% |
| Comparative Example 7 | 236.9 | 210.2 | 88.7% | 33% |
| Comparative Example 8 | 233.6 | 209.6 | 89.7% | 51% |
| Comparative Example 9 | 234.6 | 207.0 | 88.2% | 64% |

Referring to Tables 4 and 5, the batteries of Examples having 100-8000 ppb of the thiosulfate anion on a surface of the lithium metal oxide particle showed greater charging/discharging efficiency and capacity retention than those of the batteries of Comparative Examples.

The batteries of Examples showed the initial discharging capacity in a range from 210.5 mAh/g to 212 mAh/g, and the initial efficiency of about 90%. However, in the battery of Comparative Example 9 having the content of the thiosulfate anion greater than 8000 ppb, the initial discharging capacity and the initial efficiency were drastically decreased. That is, electrical stability of the lithium metal oxide particle was deteriorated due to an excessive thiosulfate anion coating and an charging/discharging efficiency was also degraded.

Further, the batteries of Examples showed improved life-span properties in a range from 63% to 67%. However, in the battery of Comparative Examples 7 and 8 having the content of the thiosulfate anion less than 100 ppb, life-span properties were decreased. That is, stability at the surface and an inside of the cathode active material particles were enhanced by a combination of the thiosulfate anion to increase capacity retentions.

Figure 3:
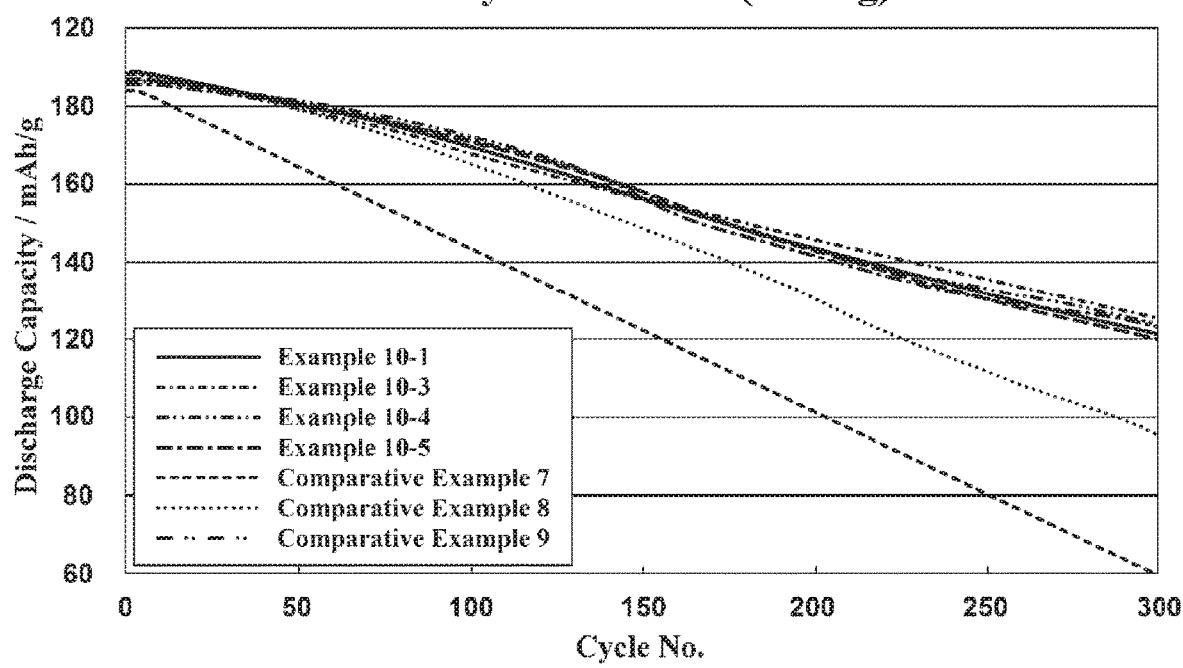
FIGS. 3 and 4 are graphs showing electro-chemical properties of lithium secondary batteries including lithium metal oxides according to Examples and Comparative Examples.
Figure 4:
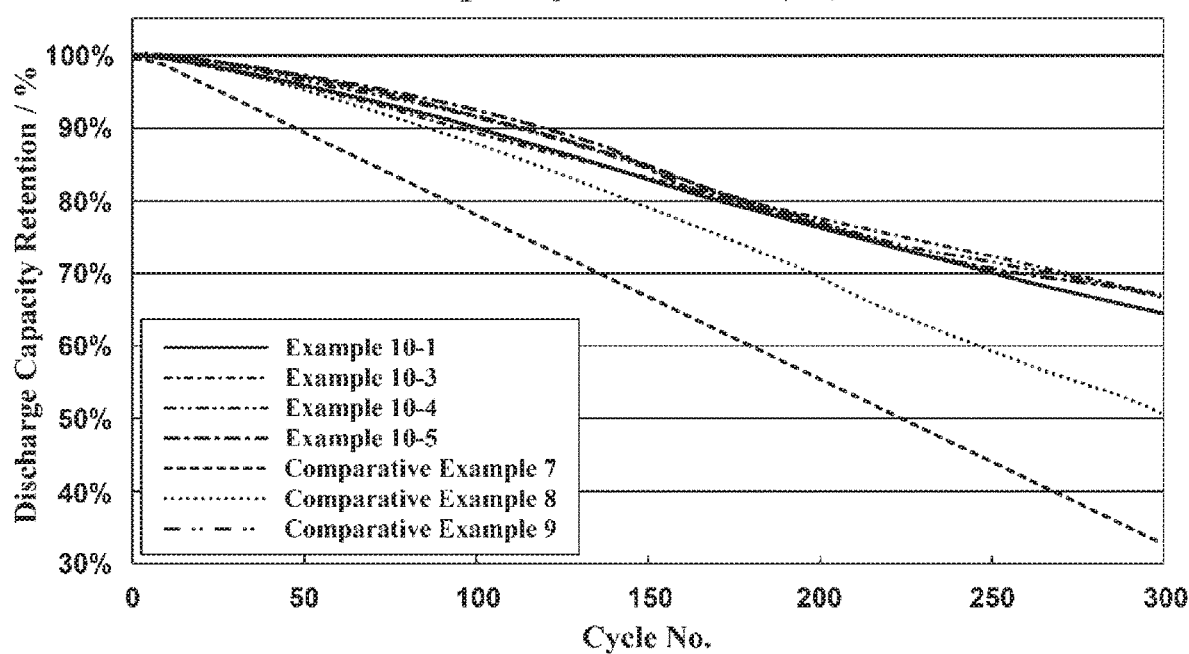

FIGS. 3 and 4 are graphs showing electro-chemical properties of lithium secondary batteries including lithium metal oxides according to Examples and Comparative Examples.

Specifically, FIG. 3 is a graph showing capacity changes during 300 cycles of charging and discharging in Examples 10-1 to 10-5 and Comparative Examples 7 to 9. FIG. 4 is a graph showing capacity retentions during 300 cycles of charging and discharging in Examples 10-1 to 10-5 and Comparative Examples 7 to 9.

Referring to FIGS. 3 and 4, in the batteries of Examples, substantially, constant capacity properties were maintained while performing 100 cycles.

(3) TOF-SIMS Analysis

Surfaces of the lithium metal oxide surfaces were analyzed using a TOF-SIMS (ION-TOF GmbH, Germany) apparatus equipped with $Bi^{3+}$ ion gun. Electrodes fabricated using the cathode active materials of Comparative Example 7 and Example 10-4 were attached to a measuring substrate, degassed for 30 minutes or more, and then vacuumed under a pressure of $10^{-9}$ mBar or less to remove impurities. Subsequently, a secondary ion mass spectrum was achieved in an area 50*50 $\mu m^2$ for 800 seconds.

Figure 5:
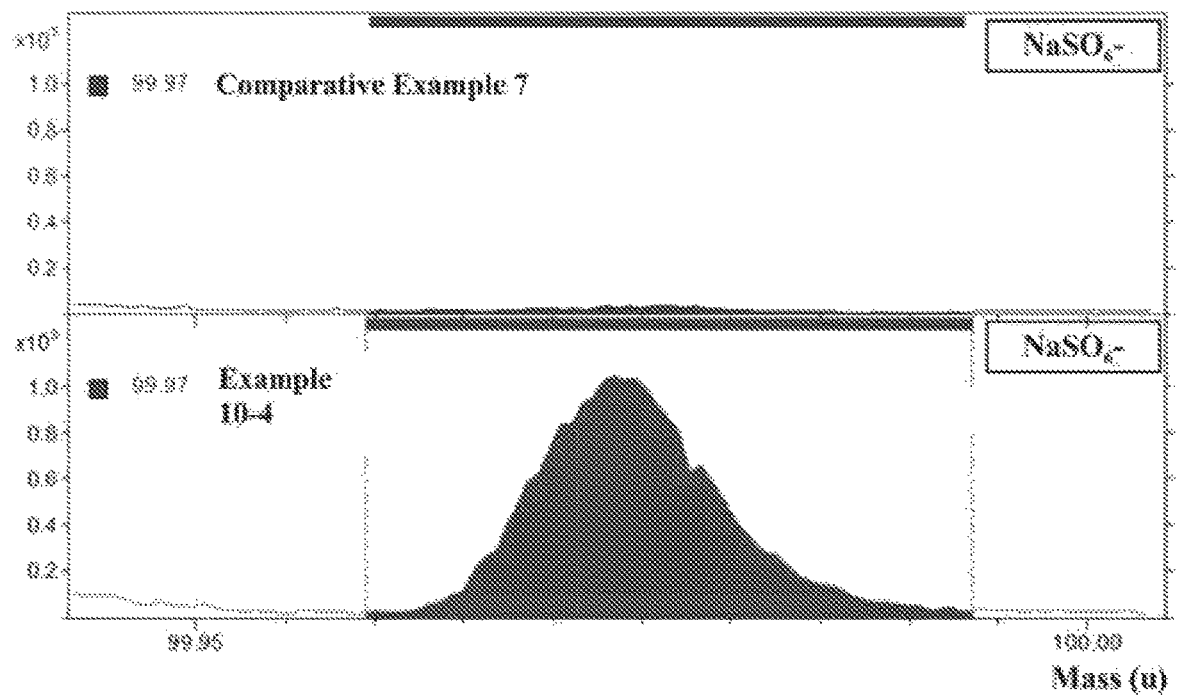
FIGS. 5 and 6 are graphs showing TOF-SIMS (Time Of Flight-Secondary Ion Mass Spectrometry) analysis results of cathode active materials of Comparative Example 7 and Example 10-4.
Figure 6:
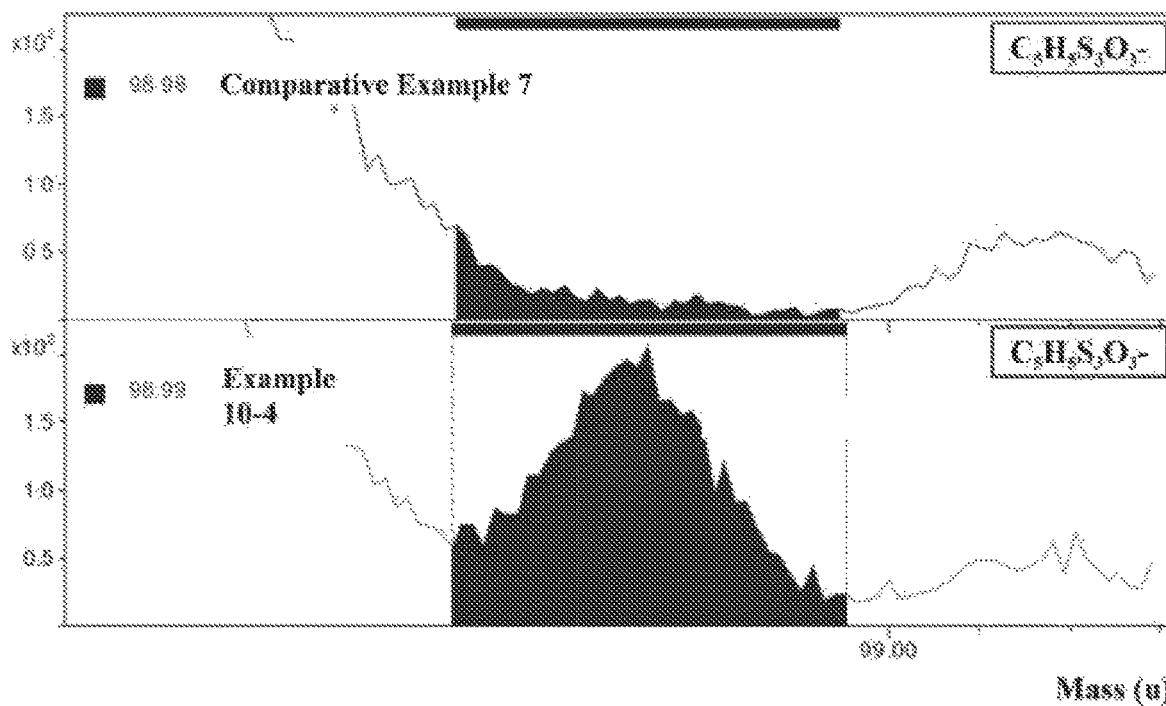

FIGS. 5 and 6 are graphs showing TOF-SIMS (Time Of Flight-Secondary Ion Mass Spectrometry) analysis results of cathode active materials of Comparative Example 7 and Example 10-4.

Specifically, FIG. 5 is graph showing an intensity of $NaSO_6{}^-$. FIG. 6 is graph showing an intensity of $C_5H_5S_3O_3{}^-$. It is confirmed or acknowledged that the thiosulfate anions were combined with at least a portion of the surface of the lithium metal oxide particle according to Example 10-4.

What is claimed is:

1. A cathode active material for a lithium secondary battery, comprising:
   a lithium metal oxide particle; and
   a thio-based compound formed on at least portion of a surface of the lithium metal oxide particle, the thio-based compound including a thioamide compound represented by Structural Formula 1,
   wherein the thio-based compound forms a coating layer, a ligand bond or a complex bond on the surface of the lithium metal oxide particle:

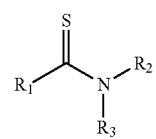

[Structural Formula 1]

wherein, in the Structural Formula 1 above, $R_1$ represents hydrogen, halogen, a salt containing $O^-$ or $S^-$, a C1-C10 hydrocarbon group capable of substituted with a substituent group, a C1-C10 alkoxy group, an amine group, an amine group substituted with a C1-C10 alkyl group, a C1-C10 thioalkyl group or a thioamide group, wherein $R_2$ and $R_3$ are each independently hydrogen or a C1-C10 hydrocarbon group capable of substituted with a substituent group, $R_2$ and $R_3$ are capable of being fused together to form a ring, and wherein the substituent group capable of being combined with $R_1$, $R_2$ and $R_3$ includes halogen, a cyano group, a hydroxyl group or a carboxyl group.

2. The cathode active material for a lithium secondary battery according to claim 1, wherein the salt containing O⁻ or S⁻ included in $R_1$ is a salt with an alkaline metal cation, an alkaline earth metal cation, $N^+R_4$ or $P^+R_4$, and $R_4$ is hydrogen or a C1-C8 alkyl group.

3. The cathode active material for a lithium secondary battery according to claim 1, wherein the hydrocarbon group included in $R_1$, $R_2$ and $R_3$ is substituted or connected by at least one selected from a group consisting of a carbon-carbon double bond, —O—, —S—, —CO—, —OCO—, —SO—, —CO—O—, —O—CO—O—, —S—CO—, —S—CO—O—, —CO—NH—, —NH—CO—O—, —NH'—, >P=O, —S—S— and —SO₂—, and R' is hydrogen or a C1-C8 alkyl group.

4. The cathode active material for a lithium secondary battery according to claim 1, wherein the thioamide compound includes at least one selected from a group consisting of compounds represented by Chemical Formulae 1 to 19:

[Chemical Formula 1]

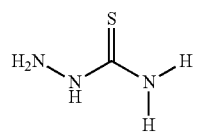

[Chemical Formula 2]

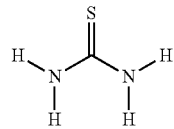

[Chemical Formula 3]

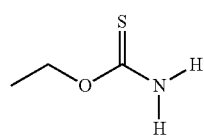

[Chemical Formula 4]

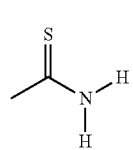

[Chemical Formula 5]

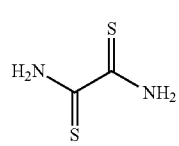

[Chemical Formula 6]

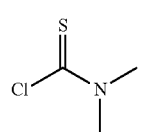

[Chemical Formula 7]

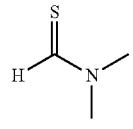

[Chemical Formula 8]

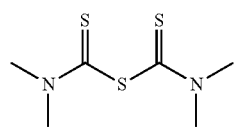

-continued

[Chemical Formula 9]

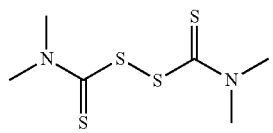

[Chemical Formula 10]

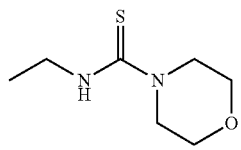

[Chemical Formula 11]

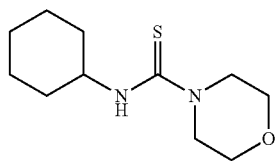

[Chemical Formula 12]

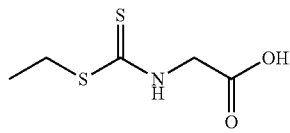

[Chemical Formula 13]

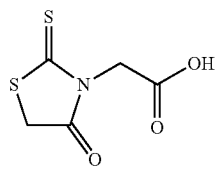

[Chemical Formula 14]

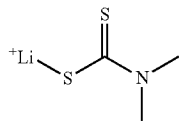

[Chemical Formula 15]

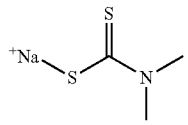

[Chemical Formula 16]

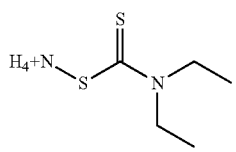

[Chemical Formula 17]

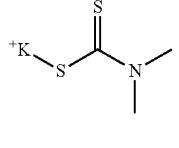

[Chemical Formula 18]

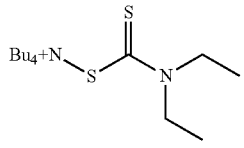

[Chemical Formula 19]

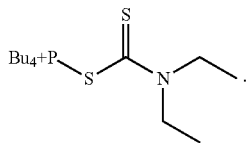

5. The cathode active material for a lithium secondary battery according to claim 1, wherein the lithium metal oxide particle includes a nickel-based lithium oxide represented by General Formula 1 below:

$$Li_xNi_yM_{1-y}O_2 \quad \text{[General Formula 1]}$$

wherein, in the General Formula 1 above, 0.95≤x≤1.08, y≥0.5, and M is at least one element selected from a group consisting of Co, Mn, Al, Zr, Ti, B, Mg or Ba.

6. The cathode active material for a lithium secondary battery according to claim 5, wherein, in the General Formula 1, 0.8≤y≤0.93.

7. The cathode active material for a lithium secondary battery according to claim 5, wherein, in the General Formula 1, M includes Co and Mn.

8. The cathode active material for a lithium secondary battery according to claim 5, wherein the lithium metal oxide particle includes a doping or a coating which contains at least one of Al, Zr or Ti.

9. The cathode active material for a lithium secondary battery according to claim 1, wherein the lithium metal oxide particle has a layer structure, and a grain boundary at a surface portion of the lithium metal oxide particle is coated by the thio-based compound.

* * * * *